(12) United States Patent
Raulerson

(10) Patent No.: US 6,939,328 B2
(45) Date of Patent: Sep. 6, 2005

(54) DISSOLVABLE SUBCUTANEOUS CATHETER COVER

(75) Inventor: J. Daniel Raulerson, Brewton, AL (US)

(73) Assignee: Medical Components, Inc., Harleysville, PA (US)

(*) Notice: Subject to any disclaimer, the term of this patent is extended or adjusted under 35 U.S.C. 154(b) by 140 days.

(21) Appl. No.: 10/374,834

(22) Filed: Feb. 26, 2003

(65) Prior Publication Data

US 2003/0163145 A1 Aug. 28, 2003

Related U.S. Application Data

(60) Provisional application No. 60/360,154, filed on Feb. 27, 2002.

(51) Int. Cl.⁷ ................................................ A61M 5/32
(52) U.S. Cl. ................................. 604/175; 606/195
(58) Field of Search .................... 604/93.01, 96.01, 604/103.05, 171, 263, 268, 523, 533–536, 285–287, 915, 104, 175; 606/192, 195, 108, 154, 194

(56) References Cited

U.S. PATENT DOCUMENTS 2,603,217 A * 7/1952 McShirley ................. 604/265
3,736,939 A * 6/1973 Taylor ........................ 604/265
4,266,999 A   5/1981 Baier
4,278,092 A   7/1981 Borsanyi et al.
4,838,280 A * 6/1989 Haaga ........................ 600/564
5,049,140 A   9/1991 Brenner et al.
5,195,988 A   3/1993 Haaga
5,334,166 A   8/1994 Palestrant
5,573,518 A   11/1996 Haaga
5,599,311 A   2/1997 Raulerson
5,630,804 A   5/1997 Imada et al.
6,113,581 A   9/2000 Levy
6,398,758 B1   6/2002 Jacobsen et al.

OTHER PUBLICATIONS

International Search Report, mailed Aug. 13, 2003.

* cited by examiner

Primary Examiner—LoAn H. Thanh
(74) Attorney, Agent, or Firm—Joseph E. Maenner; Monte & McGraw, P.C.

(57) ABSTRACT

A subcutaneous cover for insertion within a body of a user is disclosed. The cover is adapted to extend over at least a portion of a medical device disposed within the body of the user, and wherein the cover is dissolvable in the body of the user. Further, a method of subcutaneously inserting the cover into the body is also disclosed.

19 Claims, 4 Drawing Sheets

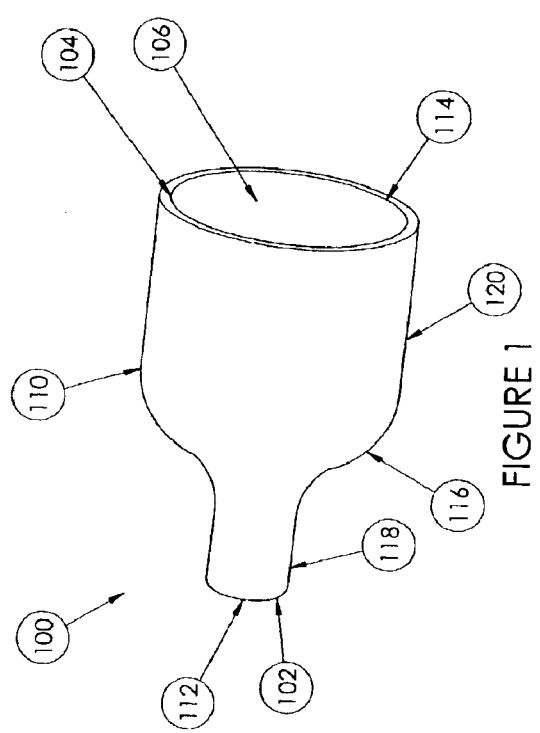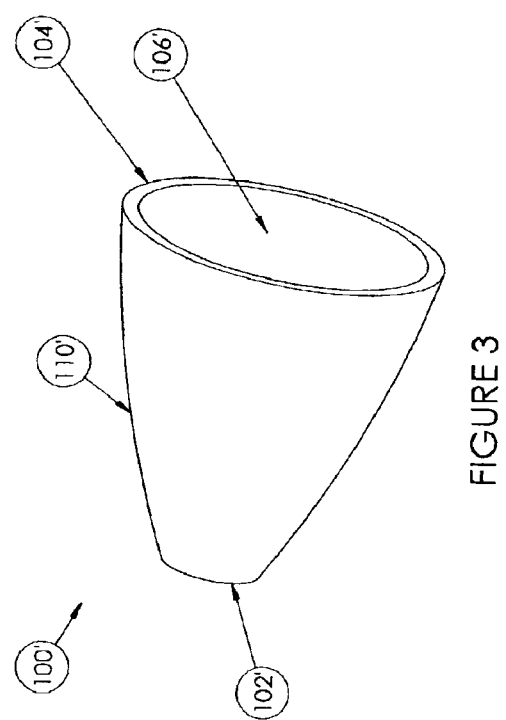

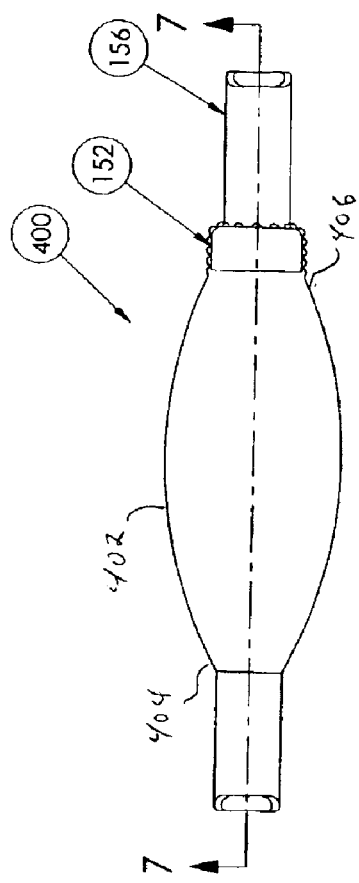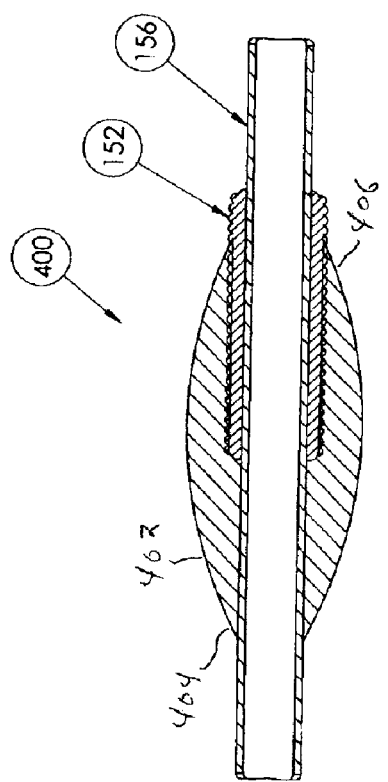

DISSOLVABLE SUBCUTANEOUS CATHETER COVER

CROSS-REFERENCE TO RELATED APPLICATION

The present application claims priority from U.S. Provisional Patent Application Ser. No. 60/360,154, filed Feb. 27, 2002, which is incorporated herein by reference.

FIELD OF THE INVENTION

The present invention relates to a covering to assist in inserting a portion of a catheter assembly into a subcutaneous tunnel.

BACKGROUND OF THE INVENTION

Catheters for the introduction or removal of fluids may be located in various venous locations and cavities throughout the body of a patient for introduction of fluids to the body or removal of fluids from the body. Such catheterization may be performed by using a single catheter having multiple lumens. A typical example of a multiple lumen catheter is a dual lumen catheter in which one lumen introduces fluid and the other lumen removes fluid. An example of such a catheter assembly is the ASH SPLIT-CATH® catheter. Catheterization may also be performed by using separate, single lumen catheters inserted through two different incisions into an area to be catheterized. An example of such a catheter assembly is a TESIO® catheter.

Generally, to insert any catheter into a blood vessel, the vessel is identified by aspiration with a long hollow needle in accordance with the well known Seldinger technique. When blood enters a syringe attached to the needle, indicating that the vessel has been found, a thin guide wire is then introduced, typically through a syringe needle or other introducer device into the interior of the vessel. The introducer device is then removed, leaving the end portion of the guide wire that has been inserted into the vessel within the vessel, and the opposing end of the guide wire projecting beyond the surface of the skin of the patient. At this point, several options are available to a physician for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire. For example, this technique may be used to insert small diameter dual lumen catheters into a patient. If the catheter to be inserted is significantly larger than the guide wire, a dilator device is passed over the guide wire to enlarge the hole. The dilator device is then removed, and the catheter is then passed over the guide wire into the vessel. The guide wire is then removed.

For chronic catheterization, in which the catheter is intended to remain inside the patient for an extended period of time, such as for weeks or even months, it is typically desired to subcutaneously tunnel the catheter using various tunneling techniques. The catheter is typically tunneled into the patient prior to inserting the catheter into the patient's vein. The catheter typically includes a cuff on the exterior of a portion of the catheter lumen that is inserted partially through, but remains in, the tunnel. The cuff is generally constructed from a fabric material, such as DACRON®, to allow the subcutaneous tissue forming the tunnel to grow into the cuff, thus securing the cuff and the catheter within the tunnel. Examples of such cuffs are disclosed in U.S. Pat. Nos. 5,509,902, 5,599,311, and 5,944,732, all of which are incorporated herein by reference. However, the cuff typically extends from the exterior of the lumen rather abruptly, which may lead to contusions or tears at the entrance to or along the tunnel, causing injury to the patient. The abrupt change also causes significant resistance to the passage of the catheter. It would be beneficial to provide a device that provides a gradual expansion between the catheter lumen and the cuff, in order to reduce the risk of injury to the patient.

BRIEF SUMMARY OF THE INVENTION

Briefly, the present invention provides a subcutaneous cover for insertion within a body of a user, wherein the cover is adapted to extend over at least a portion of a medical device disposed within the body of the user, and wherein the cover is dissolvable within the body of the user.

Additionally, the present invention provides a medical device assembly comprising a protruding portion and a cover formed over the protruding portion, wherein the cover is shaped to facilitate insertion of the cover and the protruding portion into a subcutaneous area of a body of a user, and wherein the cover is dissolvable within the body of the user.

Further, the present invention provides a method of subcutaneously inserting a medical device assembly into a body of a user, wherein the medical device assembly comprises a protruding portion, wherein the method comprises forming a subcutaneous tunnel in the body of the user; disposing a cover over the protruding portion, wherein the cover is dissolvable within the body of the user; inserting the medical device assembly, the protruding portion, and the cover into the subcutaneous tunnel, wherein at least the protruding portion and the cover remain in the subcutaneous tunnel; and allowing the cover to dissolve within the subcutaneous tunnel.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is a perspective view of a first embodiment of a cover according to the present invention.

FIG. 3 is a perspective view of a cover according to a second embodiment of the present invention.

FIG. 6 is a side elevational view of a cover according to a fifth embodiment of the present invention disposed over a catheter assembly.

FIG. 7 is a sectional view of the cover and catheter assembly taken along line 7—7 of FIG. 6.

DETAILED DESCRIPTION OF THE INVENTION

Figure 2:
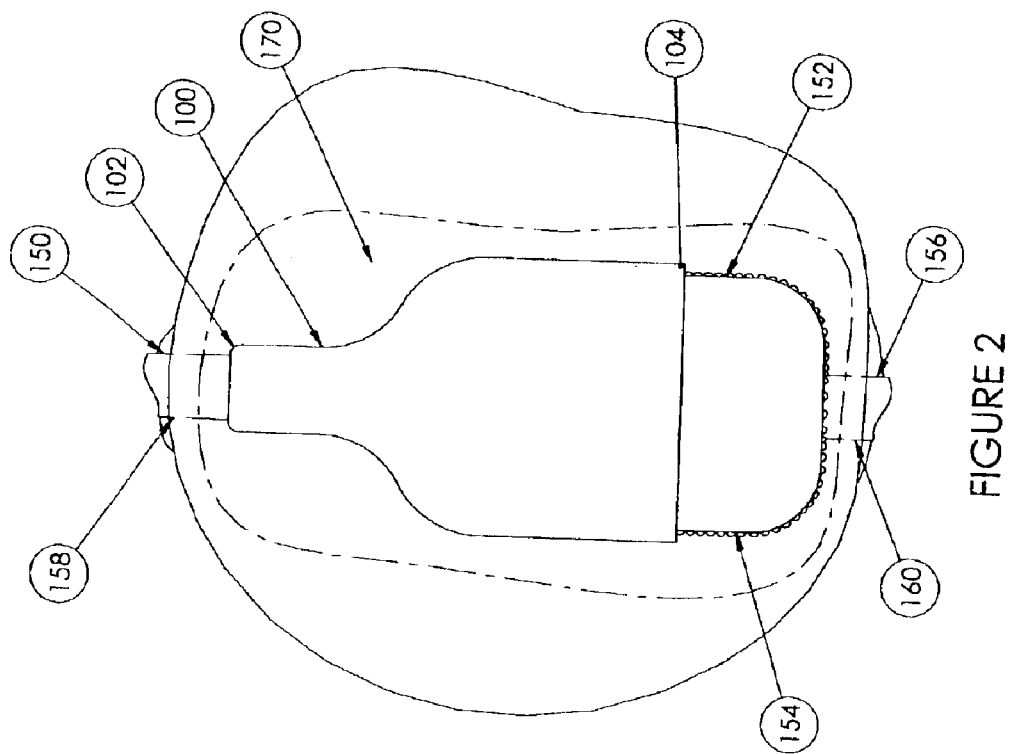
FIG. 2 is a side elevational view, partially broken away, of the cover of FIG. 1 disposed over a catheter assembly and inserted within a subcutaneous tunnel in a body.

In the drawings, like numerals indicate like elements throughout. As used in this specification, the terms "proximal" and "distal" refer to directions away from and closer to, respectively, the insertion tip of the catheter in the catheter assembly according to the present invention. Further, as used in this specification, the terms "dissolvable" and "absorbable", in addition to their commonly accepted meanings, also mean "metabolizable, disbursable and/or excretable, over a period of time, in a living organism". The terminology includes the words above specifically mentioned, derivatives thereof, and words of similar import. The following describes preferred embodiments of the invention. However, it should be understood based on this disclosure, that the invention is not limited by the preferred embodiments described herein.

Referring to FIG. 1, a first embodiment of the present invention includes a cover 100 that is adapted to be inserted subcutaneously into a body of a patient. The cover 100 is preferably adapted to be used with a catheter assembly 150, shown in FIG. 2, although those skilled in the art will recognize that the cover 100 may be used with any other medical device that is subcutaneously implanted in the body of a patient.

Referring to FIGS. 1 and 2, the cover 100 includes a tapered leading end 102 and a trailing end 104. A passageway 106 is disposed through the cover 100 between the leading end 102 and the trailing end 104. Preferably, the cover 100 has a generally tubular or funnel-shaped body 110 with a first opening 112 for the passageway 106 at the leading end 102 and a second opening 114 for the passageway 106, larger than the first opening 112, at the trailing end 104. The passageway 106 is sized to allow at least a portion of the catheter 150 to pass therethrough, such that a protruding portion 152 is retained within the passageway 106.

The body 110 is preferably shaped so that the protruding portion 152 is larger than the first opening 112 but smaller than the second opening 114, with a generally tapered funnel 116 between the leading end 102 and the trailing end 104. As shown in FIGS. 1 and 2, the funnel 116 is disposed between two generally straight tubular portions 118, 120. The generally tapered shape of the leading end 102 provides a smooth engagement of the cover 100 through the skin and the inside walls of a subcutaneous tunnel 170, so that the cover 100 does not snag the skin or the walls of the subcutaneous tunnel 170 as the cover 100 is being drawn through the subcutaneous tunnel 170. The tapered funnel 116 expands the subcutaneous tunnel 170 to allow the protruding portion 152 to be pulled through the subcutaneous tunnel 170. Further, the cover 100 protects the protruding portion 152 from the effects of being pulled and/or pushed through the generally tight-fitting subcutaneous tunnel 170. The nature of the protection provided by the cover 100 to the protruding portion 152 depends on the nature of the protruding portion 152. The protection may include, but is not limited to, preventing blockage of the protruding portion 152 from moving through the subcutaneous tunnel 170 into place therein; preventing the protruding portion 152 from slipping with respect to the catheter 150; preventing damage to the protruding portion 152 as it moves through the subcutaneous tunnel 170 into place therein, and preventing damage to the catheter 150 as it moves through the subcutaneous tunnel 170 into place therein. Additionally, the cover 100 may facilitate the lubrication of the protruding portion 152.

Referring to FIG. 2, preferably, the protruding portion 152 is an ingrowth cuff 154, although those skilled in the art will recognize that the protruding portion 152 may be other portions of a medical device, such as a port, a hub, or any other portion that protudes from the medical device and is retained within a subcutaneous tunnel.

The ingrowth cuff 154 is disposed along a lumen 156 of the catheter assembly 150 between first and second ends 158, 160, respectively, of the catheter assembly 150. The ingrowth cuff 154 may be permanently affixed to the lumen 156, or the ingrowth cuff 154 may be a clamshell cuff as disclosed in U.S. Pat. Nos. 5,509,902 and 5,599,311, which is affixed to the catheter lumen 156 at a location determined by the physician inserting the catheter 150. The ingrowth cuff 154 has a cross-sectional diameter that is larger than the cross-sectional diameter of the lumen 156, such that the ingrowth cuff 154 protrudes outwardly from the lumen 156. Without the cover 100 of the present invention, during tunneling of the lumen 156 through the subcutaneous tunnel 170, the ingrowth cuff 154 may snag on the skin and/or the subcutaneous tissue of the tunnel 170, causing injury to the body of the patient. While the cover 100 shown in FIG. 2 does not completely encompass the protruding portion 152, those skilled in the art will recognize that the cover 100 may be elongated to encompass the entire protruding portion.

The cover 100 is constructed from a material that is dissolvable and/or absorbable by the body of the patient so that, over a period of time; the cover 100 is no longer present around the protruding portion 152, allowing repair cells in the subcutaneous tissue forming the subcutaneous tunnel 170 to grow around the protruding portion 152. Preferably, the dissolution and/or the absorption period is on the order of several hours, the actual time period depends upon several factors, including but not limited to, the material used, the thickness of the material, and the metabolism of the person in whose skin the cover 100 is inserted. Those skilled in the art will recognize that various time periods for the dissolution and/or absorption of the cover 100 are contemplated by the present invention.

Upon dissolution and/or absorption of the cover 100 by the body, the material from which the cover 100 was constructed, that cannot be used by the body, is excreted from the body by the kidneys. In a body in which the kidneys do not properly or sufficiently function, the dissolved and/or absorbed material is removed from the body by dialysis.

While any biocompatible material that is dissolvable and/or absorbable within a living body may be used, the cover 100 may preferably be constructed from an interlinked polyalkylene glycol as disclosed in U.S. Provisional Patent Application filed by Shalaby Shalaby entitled "Interlinked Solid Polyethylene Glycols and Copolymers Thereof", filed Feb. 27, 2002, and which is incorporated herein by reference. The interlinked polyalkylene glycol, as disclosed by Dr. Shalaby, is an interlinked glycol with an overall molecular weight of more than 50,000 Daltons (Da), which also absorbs and readily generates polyethylene by-products having a molecular weight of 10,000 Da or less. The cover 100 may be constructed from Dr. Shalaby's disclosed interlinked polyalkylene glycol formed of a polyalkylene glycol and interlinking ester or carbonate groups having a molecular weight of at least about 30,000 Da and a melting temperature of at least about 50° C. Also, the interlinked polyakylene glycol used may have a molecular weight of at least about 8,000 Da. Using these compositions, the cover 100 may be compression molded or extruded.

Alternatively, the cover 100 may be constructed from at least one of solutions of sucrose, mannitol or sorbitol; mucoid substances, pectins, gels, soluble starches, algenic acid, hydrated gels, dextrans, dextranes, dextrins, polyethylene glycol, polyethylene oxide, polypropylene oxide, polyvinylpyrrolidine, polyvinyl acetate, polyvinyl alcohol, sugar alcohol; carbohydrates such as starch and sugars; polysaccharides such as mannitol, maltitol, sorbitol, xsylitol, fructose, sucrose, dextrose, glucose, glucosamine, lactose, anionic hydrated polysaccharides such as gellan, curdlan, XM-6, xanthan; seaweed polysaccharides such as agar, algin, cattageenan, furcelleran; cellulose derivatives such as alkyl cellulose, hydroxymethyl cellulose; various salts such as sodium chloride, potassium chloride, and sodium carbonate; acetates; gums including gum arabic and tragacanth gum; gelatin, and methyl cellulose, as well as any combinations of the above-mentioned materials.

Further, the material that comprises the cover 100 may be optionally doped, laced, or coated with a medicament, such as an antibiotic, to reduce the risk of infection around the ingrowth cuff 154 after the cover 100 dissolves. Alternatively, the medicament may be a painkiller or anti-inflammatory drug, to reduce the pain and/or swelling in the tissue around the subcutaneous tunnel 170.

To use the cover 100, the cover 100 is disposed over the protruding portion 152 on the catheter lumen 156 such that the leading end 102 of the cover 100 leads the cover 100 as the catheter lumen 156 is drawn through the subcutaneous tunnel 170. The subcutaneous tunnel 170 is formed within the skin of the body of the user according to methods well known to those skilled in the art. The catheter lumen 156 is pulled and/or pushed through the subcutaneous tunnel 170 until at least the cover 100 and the protruding portion 152 remain within the subcutaneous tunnel 170. Over a period of time, preferably just a few hours, the cover 100 dissolves or is absorbed into the body of the user. After the cover 100 dissolves, the skin forming the subcutaneous tunnel 170 grows around the protruding portion 152, securing the protruding portion 152, and thus the catheter 150, within the subcutaneous tunnel 170.

An alternative embodiment of the invention is shown in FIG. 3. Here, an inventive cover 100', which is similar to the cover 100, includes a body 110' having a leading end 102' and a trailing end 104'. A passageway 106' extends through the body 110' between the leading end 102' and the trailing end 104'. The body 110' has a first opening 112' for the passageway 106' at the leading end 102' and a second opening 114' for the passageway 106', preferably larger than the first opening 112' at the trailing end 104'. The body 110', while tapering from smaller to larger from the leading end 102' toward the trailing end 104', tapers generally constantly between the leading end 102' and the trailing end 104'. The cover 100' is preferably constructed from any of the materials described above, with the molecular weight described above, and dissolves within the body of the user over a period of time. The cover 100' is used in the same manner described above for the cover 100.

As seen in the covers 100 and 100' as shown in FIGS. 1 and 3, covers envisioned by the present invention may be different shapes with different tapers, but taper generally from smaller to larger from a leading end toward a trailing end of the cover. For example, other shapes, such as a teardrop shape, fall within the scope and intent of the present invention, as well.

Figure 4:
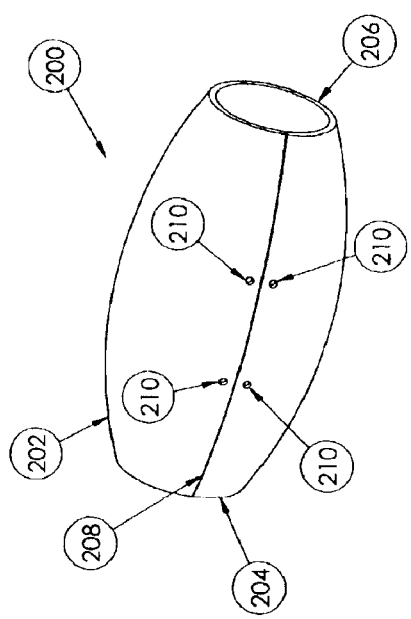
FIG. 4 is a perspective view of a cover according to a third embodiment of the present invention.

Cover 200, another alternative embodiment of the invention, is shown in FIG. 4. The cover 200 includes a body 202 having a first end 204, a second end 206, and a passageway 212 that extends through the body 202 between the first end 204 and the second end 206. The body 202 has a first opening 214 for the passageway 212 at the first end 204 and a second opening 216 for the passageway 212 at the second end 206. The body 202 also has a longitudinal side opening 208 that extends from the first end 204 to the second end 206. The side opening 208 allows the cover 200 to be opened along the side opening 208 to allow the medical device 150 with the protruding portion 152 to be inserted laterally through the side opening 208. Optionally, at least one suture opening 210 may be disposed on either side of the side opening 208 to allow the side opening 208 to be sutured closed with sutures (not shown) after insertion of the protruding portion 152 within the cover 200. The sutures are preferably constructed from a material that is absorbable and/or dissolvable within the body, although those skilled in the art will recognize that the sutures need not necessarily be absorbable and/or dissolvable within the body. Although two suture openings 210 are shown on either side of the side opening 208, those skilled in the art will recognize that more or less than two suture openings 210 may be disposed along the side opening 208.

While the body 202 as shown in FIG. 4 is generally football shaped, those skilled in the art will recognize that the body 202 may be other shapes, as long as the protruding portion 152 is able to fit within the body 202. The cover 200 is preferably constructed from any of the materials described above, with the molecular weight described above, and dissolves within the body of the user over a period of time. The cover 200 is used in the manner described above for the cover 100, except that the cover 200 is placed laterally over a medical device, such as the protruding portion 152 shown in FIG. 2, by inserting the protruding portion 152 through the side opening 208.

Figure 5:
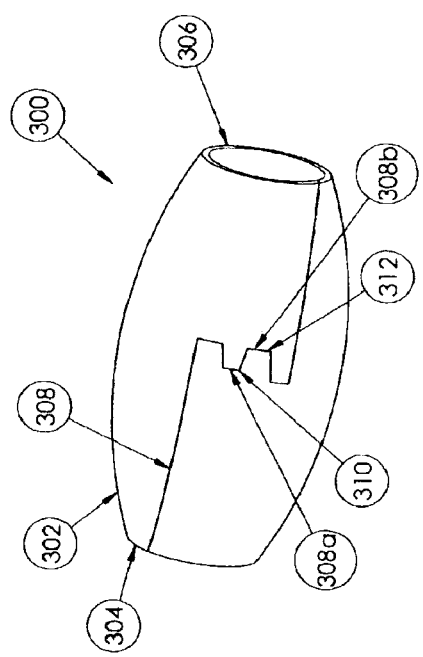
FIG. 5 is a perspective view of a cover according to a fourth embodiment of the present invention.

Cover 300, another alternative embodiment of the invention, is shown in FIG. 5. The cover 300 includes a body 302 having a first end 304, a second end 306, and a passageway 314 that extends through the body 302 between the first end 304 and the second end 306. The body 302 has a first opening 316 for the passageway 314 at the first end 304 and a second opening 318 for the passageway 314 at the second end 306. A generally longitudinal side opening 308 extends along the body 302 from the first end 304 to the second end 306. A first interlocking member 310 extends along a first side 308a of the side opening 308, while a complementary second interlocking member 312 extends along a second side 308b of the side opening 308. The side opening 308 allows the cover 300 to be opened along the side opening 308 to allow the medical device 150 with the protruding portion 152 to be inserted through the side opening 308. After the protruding portion 152 is disposed within the cover 300, the first and second interlocking members 310, 312 retain the first and second sides 308a, 308b, respectively, together to securely close the side opening 308. The cover 300 is preferably constructed from any of the materials described above, with the molecular weight described above, and dissolves within the body of the user over a period of time. The cover 300 is used in substantially the same manner as the cover 200 as described above.

In another alternative embodiment, as shown in FIGS. 6 and 7, a cover 400 is applied to the protruding portion 152 in a liquid, a gelatinous, or a semi-solid form and allowed to solidify around the protruding portion 152 prior to inserting the cover 400 and the protruding portion 152 into the tunnel. While the cover 400 is in the liquid, gelatinous, or semi-solid form, a mold (not shown) may be disposed around the cover 400 to form the cover 400 and give a desired shape to the cover 400. The cover 400 includes a body 402 having a leading end 404 and a trailing end 406. The body 402 tapers from a smaller to a larger size from the leading end 404 toward the trailing end 406.

Alternatively, the cover 400 may be painted over the protruding portion 152, the protruding portion 152 may be dipped in the material comprising the cover 400, or the cover 400 may otherwise applied to the protruding portion 152 in any suitable manner. The cover 400 may be any of the shapes described above, or any other suitable shape, as will be recognized by those skilled in the art. The cover 400 is preferably constructed from any of the materials described above, with the molecular weight described above, and dissolves within the body of the user over a period of time.

The cover 400 is used by forming the cover 400 around the protruding portion 152 prior to pulling and/or pushing the catheter lumen 156 having the medical device with the protruding portion 152, under the skin of the body and through the subcutaneous tunnel 170 of the patient. While the cover 400 shown in FIGS. 6 and 7 does not encompass the entire protruding portion, those skilled in the art will recognize that the cover 400 may be elongated to encompass the entire protruding portion 152.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A catheter assembly for insertion within a body of a user comprising a catheter having an ingrowth device and a subcutaneous cover comprising a cover including a first open end and a second open end, wherein the cover is sized to allow the catheter to extend through both the first and second open ends when the catheter is disposed within the body of the user, wherein the cover comprises a generally funnel-shaped body, and wherein the cover is dissolvable within the body of the user.

2. The subcutaneous cover according to claim 1, wherein the catheter assembly is constructed from polyalkylene glycol.

3. The subcutaneous cover according to claim 2, wherein the catheter assembly is further constructed from at least one of an ester and a carbonate group.

4. The subcutaneous cover according to claim 3, wherein the catheter assembly has a molecular weight of at least about 30,000 Daltons.

5. The subcutaneous cover according to claim 1, wherein the ingrowth device is a clamshell cuff.

6. The catheter assembly according to claim 1, further comprising a longitudinal side opening extending from the first open end to the second open end.

7. The catheter assembly according to claim 6, wherein the longitudinal side opening is closable with sutures.

8. The catheter assembly according to claim 7, wherein the sutures are dissolvable within the body of the user.

9. The catheter assembly according to claim 6, further comprising a plurality of interlocking members, wherein the longitudinal side opening is closable by interlocking the plurality of interlocking members.

10. A medical device assembly comprising a clamshell cuff and a cover formed over the clamshell cuff, wherein the cover includes a first open end and a second open end, wherein the cover is shaped to facilitate insertion of the cover and the clamshell cuff into a subcutaneous area of a body of a user, and wherein the cover is dissolvable within the body of the user.

11. The medical device assembly according to claim 10, wherein the medical device assembly is a catheter assembly.

12. The medical device assembly according to claim 10, wherein the cover is initially formed over the clamshell cuff in one of a liquid, gelatinous and semi-solid form.

13. The medical device assembly according to claim 10, wherein the cover is constructed from polyalkylene glycol.

14. The medical device assembly according to claim 13, wherein the subcutaneous cover is further constructed from at least one of an ester and a carbonate group.

15. The subcutaneous cover according to claim 14, wherein the cover has a molecular weight of at least about 30,000 Daltons.

16. A method of subcutaneously inserting a medical device assembly into a body of a user, wherein the medical device assembly comprises a protruding portion, wherein the method comprises:

forming a subcutaneous tunnel in the body of the user;

disposing a cover over the protruding portion, wherein the cover is dissolvable within the body of the user;

inserting the medical device assembly, the protruding portion, and the cover into the subcutaneous tunnel, wherein at least the protruding portion and the cover remain in the subcutaneous tunnel; and allowing the cover to dissolve within the subcutaneous tunnel.

17. The method according to claim 16, wherein the protruding portion comprises an ingrowth cuff, and the method further comprises, after allowing the cover to dissolve within the subcutaneous tunnel, allowing the body of the user to grow around the ingrowth cuff.

18. The method according to claims 16, wherein disposing the cover over the protruding portion comprises inserting the medical device assembly into the cover.

19. The method according to claim 16, wherein disposing the cover over the protruding portion comprises applying at least one of a liquid, gelatinous, and semi-solid compound over the protruding portion and allowing the at least one of the liquid, gelatinous, and semi-solid compound to solidify around the protruding portion prior to inserting the medical device.

* * * * *